United States Patent
Åström et al.

(10) Patent No.: US 8,923,599 B2
(45) Date of Patent: Dec. 30, 2014

(54) METHOD AND ARRANGEMENT IN A MEASURING SYSTEM

(75) Inventors: Anders Åström, Linköping (SE); Erik Åstrand, Färjestaden (SE)

(73) Assignee: Sick IVP AB, Linkoping (SE)

( * ) Notice: Subject to any disclaimer, the term of this patent is extended or adjusted under 35 U.S.C. 154(b) by 1896 days.

(21) Appl. No.: 10/774,948

(22) Filed: Feb. 10, 2004

(65) Prior Publication Data

US 2004/0234118 A1    Nov. 25, 2004

Related U.S. Application Data

(63) Continuation-in-part of application No. PCT/SE02/01791, filed on Oct. 1, 2002.

(30) Foreign Application Priority Data

Oct. 2, 2001 (SE) .................................. 0103279

(51) Int. Cl.
*G06K 9/00* (2006.01)
*G01N 33/46* (2006.01)
*G01N 21/898* (2006.01)
*G01B 11/25* (2006.01)
*G01B 11/30* (2006.01)

(52) U.S. Cl.
CPC ............ *G01N 33/46* (2013.01); *G01N 21/8986* (2013.01); *G01B 11/25* (2013.01); *G01B 11/303* (2013.01)
USPC .......................................... 382/141; 382/142

(58) Field of Classification Search
USPC ..................... 382/141, 298, 301; 375/240.12; 708/709; 712/32
See application file for complete search history.

(56) References Cited

U.S. PATENT DOCUMENTS 3,719,775 A * 3/1973 Takaoka et al. ............... 348/145
3,976,384 A     8/1976 Matthews et al.
(Continued)

FOREIGN PATENT DOCUMENTS

| CA | 2335784 A1 | 8/2001 |
|---|---|---|
| EP | 1985969 | 10/2008 |

(Continued)

OTHER PUBLICATIONS

Åstrand Erik, "Automataic Inspection of Sawn Wood", Linköping Studies in Science and Technology, Dissertations No. 424, University of Linköping, 1996, pp. 51-66.

(Continued)

*Primary Examiner* — Tsung-Yin Tsai
(74) *Attorney, Agent, or Firm* — Fish & Richardson P.C.

(57) ABSTRACT

The present invention relates to a method and an arrangement for representing the characteristics of an object with a measuring system, in which either the measuring system or the object is designed to move in relation to one another in a predefined direction of movement. The object preferably is designed to move in relation to the measuring system. At least one light source is designed to illuminate the object with a light which is incident upon the object and has a limited extension in the direction of movement. An imaging sensor, which is arranged on the same side of the object as the light source is designed to pick up light reflected from the object and to convert this into electrical charges. An image-processing unit is furthermore designed to create a digital representation of the object from said electrical charges. The light source is arranged at a predetermined distance from the imaging sensor viewed in the direction of movement, and the image-processing unit is designed to simultaneously read out information on the geometric profile of the object and information on the light scatter in a predetermined area around said profile.

22 Claims, 5 Drawing Sheets

(56) References Cited

U.S. PATENT DOCUMENTS

| | | | |
|---|---|---|---|
| 4,168,489 A * | 9/1979 | Ervin | 382/301 |
| 4,188,544 A * | 2/1980 | Chasson | 250/559.06 |
| 4,826,299 A | 5/1989 | Powell | |
| 4,984,172 A | 1/1991 | Luminari | |
| 5,233,191 A * | 8/1993 | Noguchi et al. | 850/1 |
| 5,274,244 A | 12/1993 | Johansson et al. | |
| 5,327,254 A * | 7/1994 | Daher | 382/298 |
| 5,347,311 A * | 9/1994 | Golin | 375/240.12 |
| 5,487,172 A * | 1/1996 | Hyatt | 712/32 |
| 5,490,100 A * | 2/1996 | Kableshkov | 708/709 |
| 5,644,392 A | 7/1997 | Soest et al. | |
| 5,703,960 A * | 12/1997 | Soest | 382/141 |
| 5,831,748 A * | 11/1998 | Tsukada et al. | 382/169 |
| 6,037,579 A * | 3/2000 | Chan et al. | 250/216 |
| 6,064,747 A * | 5/2000 | Wills et al. | 382/100 |
| 6,094,269 A * | 7/2000 | Ben-Dove et al. | 356/623 |
| 6,097,849 A * | 8/2000 | Nevis | 382/274 |
| 6,382,515 B1 * | 5/2002 | Good et al. | 235/472.01 |
| 6,934,420 B1 * | 8/2005 | Hsu et al. | 382/252 |
| 6,971,580 B2 * | 12/2005 | Zhu et al. | 235/472.01 |
| 2004/0179719 A1 * | 9/2004 | Chen et al. | 382/118 |
| 2005/0169529 A1 * | 8/2005 | Owechko et al. | 382/190 |
| 2006/0147901 A1 * | 7/2006 | Jan et al. | 435/4 |
| 2006/0151604 A1 * | 7/2006 | Zhu et al. | 235/454 |

FOREIGN PATENT DOCUMENTS

| | | |
|---|---|---|
| JP | 5503990 A | 6/1993 |
| JP | 3231383 | 10/1995 |
| JP | 9190372 | 7/1997 |
| SE | 501650 | 4/1995 |
| WO | WO 95/24636 A1 | 9/1995 |

OTHER PUBLICATIONS

Wendt, "Stack Filters", IEEE Transactions on Acoustics, Speech, and Signal Processing, vol. ASSP-34, No. 4, Aug. 1986, pp. 898-911.

Mattias Forslund; UTVÄRDERING AV NY TEKNIK VID DIMENSIONSMÄD TNING AV SÅGTIMMER; Dec. 2000; 5 pages, and English Translation (4 pages).

"Information about project: Improved Measurement of Saw Timber," VMR, Sep. 1999, 9 pages.

"Lagesrapport for projekt 'Effektivare sagtimmertaning,'" VMR, Jun. 2000, 7 pages (with machine translation).

Astrand, "Automatic Inspection of Sawn Wood," Doctoral Thesis, University of Linkoping, 1996, 68-72.

"Projekt Effectivare sagtimmermatning—Teknikutveckling," VMR Tratek, Mar. 2000, 12 pages (with machine translation).

Forslund, "Utvardering av ny teknik vid dimensionsmatning av sagtimmer," Tratek Report P 0012041, Royal Institute of Technology, Dec. 2000, 117 pages (with English translation).

Green, "3-D Log Scanning and Optimization," 5th International Conference on Scanning Technology and Process Control for the Wood Products Industry, Atlanta, Georgia, Oct. 1993, 16 pages.

Johannesson, "Sheet-of-light Range Imaging," Licentiate Thesis, Universtiy of Linkoping, ISBN 91/7871-188-6, Nov. 1993, 24-26; 41; 47-49.

* cited by examiner

METHOD AND ARRANGEMENT IN A MEASURING SYSTEM

CROSS-REFERENCE TO RELATED APPLICATIONS

This application is a continuation-in-part of International Application No. PCT/SE02/01791 filed Oct. 1, 2002, designating the United States and claiming priority from Swedish patent application No. 0103279-6, filed Oct. 2, 2001, the entire contents of the disclosures of both of which are hereby incorporated by reference.

TECHNICAL FIELD

The present invention relates generally to a method and an arrangement for imaging the characteristics of an object and relates in particular to a method and an arrangement for imaging the characteristics of an object by means of a measuring system, in which the measuring system and/or the object are moved in relation to one another in a predefined direction of movement, the object preferably being moved in relation to the measuring system. The object is illuminated by means of incident light, which has limited extension in the direction of movement, and light reflected from the object is detected by means of an imaging sensor arranged on the same side of the object as the incident light, the imaging sensor converting the detected light into electrical charges, according to which a digital representation of the characteristics of the object is created.

DESCRIPTION OF THE PRIOR ART

D1: U.S. Pat. No. 3,976,384
D2: SE 501 650
D3: Åstrand Erik, Automatic Inspection of Sawn Wood, doctoral thesis, University of Linköping, 1996
D4: Wendt P, Coyle E, Gallagher N, Stack Filters, IEEE trans. ASSP-34, 1986

An advantageous method of detecting defects in wood is already known in the art, in which the surface of the wood is illuminated by a light source, for example a laser, and the scattering of the light in the surface layer of the wood is measured. That is to say, the light penetrating the material is registered and after scattering emerges from the material at a different location from that at which it entered. How this occurs depends on the internal characteristics of the material, which can in this way be measured. The greater part of the incident light, however, is reflected at the surface and is termed "diffuse light". A point light source [D1] or alternatively a linear light source [D2] may be used for this purpose. The detector may comprise discrete light-sensitive elements but in an advantageous embodiment a linear light source is used together with a two-dimensional image-processing sensor [D2]. It is particularly advantageous if the image-processing sensor has the facility for defining various windows, that is to say limiting the part of the image-processing sensor that is read out for further processing.

Also known is the possibility of measuring the shape of an object, that is to say the cross-sectional geometric profile thereof, by illuminating it with a light source and then detecting the position of the representation of the reflected light on a sensor, which observes the object from a given angle, so-called triangulation. This will be referred to hereinafter as profile measurement. Combining light scatter measurement and profile measurement by illuminating the wood surface with more than one light source [D2], one for light scatter and one for profile measurement, in one image is likewise known.

In the known methods of measuring light scatter, the direction of illumination from the light source and the direction of observation of the image-processing sensor lie substantially in the same plane. This means that the representation of both the reflected and the scattered light always ends up in the same position on the image-processing sensor regardless of the geometric profile of the piece of timber. This means that only a small part of the image surface needs to be read out and the measurement can thereby be performed at high frequency.

In measuring the profile, on the other hand, the representation of the reflected light and of the scattered light will quite naturally end up in different positions depending on dimensions. It is necessary here to compromise on the size of the image window and the angle of the light source in order to obtain different measuring ranges and accuracies. The greatest limitations here are the fact that large image windows give large quantities of data to be read out from the image-processing sensor for further processing, and that a large data processing capacity is required in order to perform calculations on this large quantity of image data.

When inspecting wood it is desirable to combine detection of light scatter and geometric profile. Owing to the limitations outlined above, however, it has in practice not been possible, using known methods, to obtain a measuring frequency adequate for the simultaneous measurement of light scatter and profile. Different light sources have therefore been used for these two measurements and one problem which then occurs is that these characteristics are measured at different locations at any given instant. Data from one measurement must therefore be corrected in order to spatially match the measurement from the other, and this correction can never be made one hundred percent. Furthermore, one obvious disadvantage is that a plurality of different light sources entails a higher system cost.

SUMMARY OF THE INVENTION

An object of the present invention is to provide an improved method for simultaneously acquiring geometric profile information of an object and the light scatter information in a predetermined area around said profile by means of a measuring system.

Another object is to provide an improved arrangement for simultaneously reading out the geometric profile information of an object and the light scatter information in a predetermined area around the said profile by means of a measuring system.

According to one embodiment of the present invention said objects have been achieved by a method and an arrangement according to the characterising parts of claim 1 and claim 9 respectively.

BRIEF DESCRIPTION OF THE DRAWINGS

The invention will now be described in more detail with examples of embodiments and with reference to the drawings attached, in which.

DETAILED DESCRIPTION OF EMBODIMENTS

The invention in question relates to a method for rapidly measuring light scatter (dispersion) and/or geometric profile by means of one and the same light source. In practical terms this is a method for reducing the quantity of data on or in proximity to the actual image-processing sensor in order to thereby obtain a high measuring frequency, given a limited bandwidth to a subsequent computer unit. All essential information regarding the light scatter and/or geometric profile can then be reconstructed from the reduced set.

Figure 1:
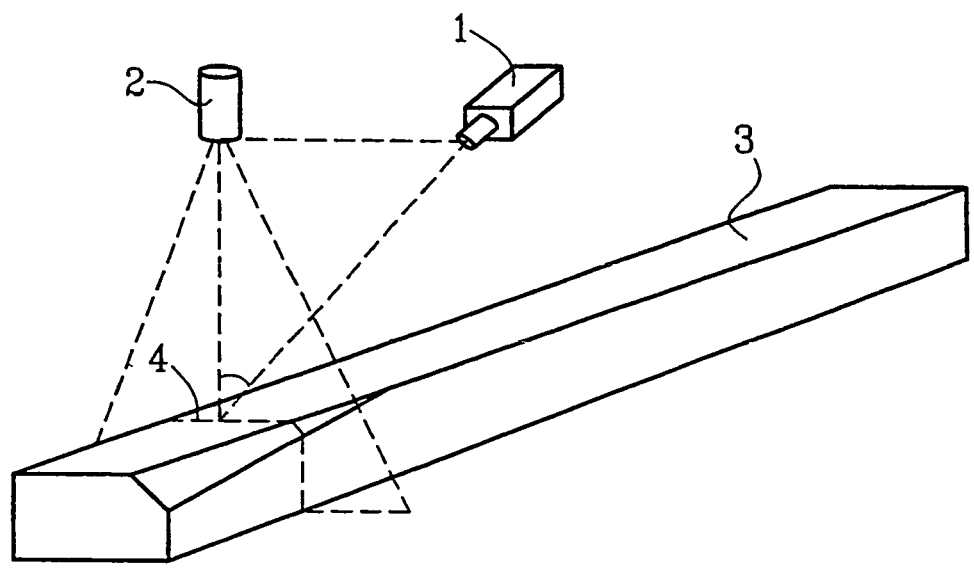
FIG. 1 shows a perspective view of an inventive measuring system.
Figure 2:
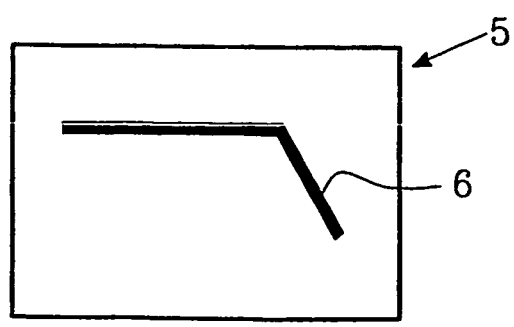
FIG. 2 shows the image of the light source reflection on the object registered in the imaging sensor.
Figure 3:
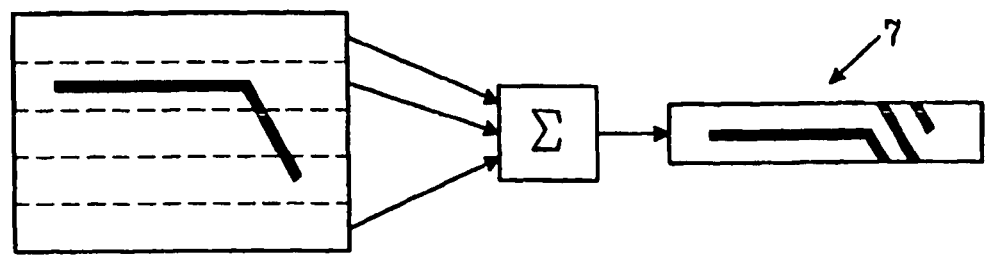
FIG. 3 illustrates how the sensor image is compressed.

The invention will now be explained with reference to the figures below. FIG. 1 shows a typical set-up with a camera 1 containing an imaging sensor, a linear light source 2, for example a laser, and an object 3, the characteristics of which are to be represented. In FIG. 1 the line on the object 3 where the light is incident is denoted by 4. Light sources other than linear ones are also feasible. FIG. 2 shows the image 5 registered by the camera in which the representation of the laser line 4 is illustrated by the line 6. Supposing now that we form a total image by adding up in columns a number of rows in the image, for example every tenth one, as illustrated in FIG. 3. In the resulting total image 7 row 1 will thereby represent the sum of rows {1, 11, 21} etc., row 2 the sum of {2, 12, 22} etc.

In the following, representation of the light source relates to the representation on the imaging sensor of the light reflected on the object and scattered in the object.

Whilst at the same time forming the summation, for each column a check is kept on the row in which the representation of the light source first became visible. This can be done, for example, by continuously comparing the total with a threshold value. If the total after adding a further row has passed the threshold value for a certain column, a note is made of the position in which this occurred. This can be done, for example, by saving the result of the threshold operation in a bit field 8. The bit field 8 contains as many bits as the number of rows added up for each row in the total image. If, for example, the first total reaches the threshold after row 31, that is to say after the third summation, bit 3 is entered in the register. If the next total reaches the threshold in row 22, that is to say after the second addition, bit 2 is entered and so on. The result when all summations are completed is not only the total image but also a vector 9 with one bit field each for each column, which can be used in order to calculate where in the original sensor image the representation of the light source was first generated. This is shown in more detail in FIG. 4. It should be noted, however, that this is only one of several possible ways of registering the position when the sum reached a certain level. The invention in no way depends on precisely how this is done.

It should be mentioned that as an alternative to summation it is also possible to use a max operation in which the greatest value in each column is retained. This actually gives a less noise sensitive result but can, on the other hand, be more expensive to implement. It depends, therefore, on the embodiment. As further alternatives, other so-called Stackfilter operations [D4] are also conceivable.

Figure 4:
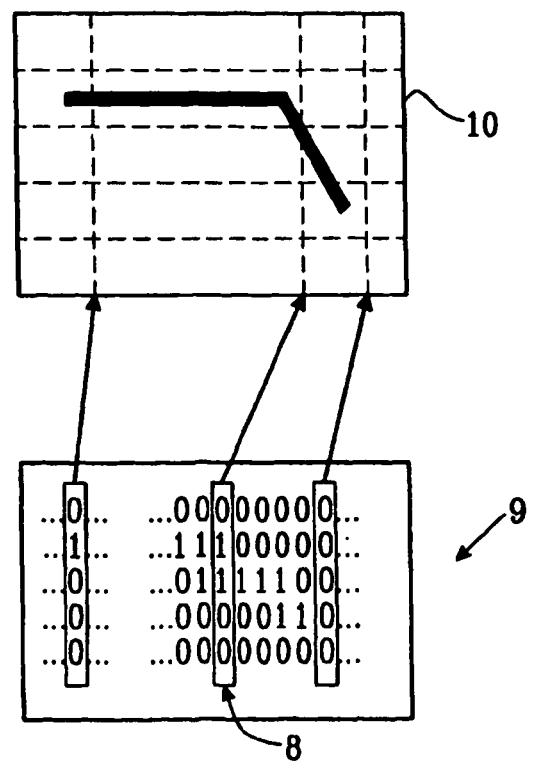
FIG. 4 illustrates an embodiment of a decoding vector used in order to reconstruct the original image.

The method when recreating data in the computer unit proceeds from the vector with bit field 9 according to the above, which gives a rough estimate of the position of the line. The bit field can be seen as giving the position of the partial window 10 in the original image which is represented by the summation image. Only those parts of the original image that contain the laser line 4 make a significant contribution. If the line lies at the boundary between two partial windows, both corresponding bits in the bit field will be set to one, as illustrated in FIG. 4.

Figure 5:
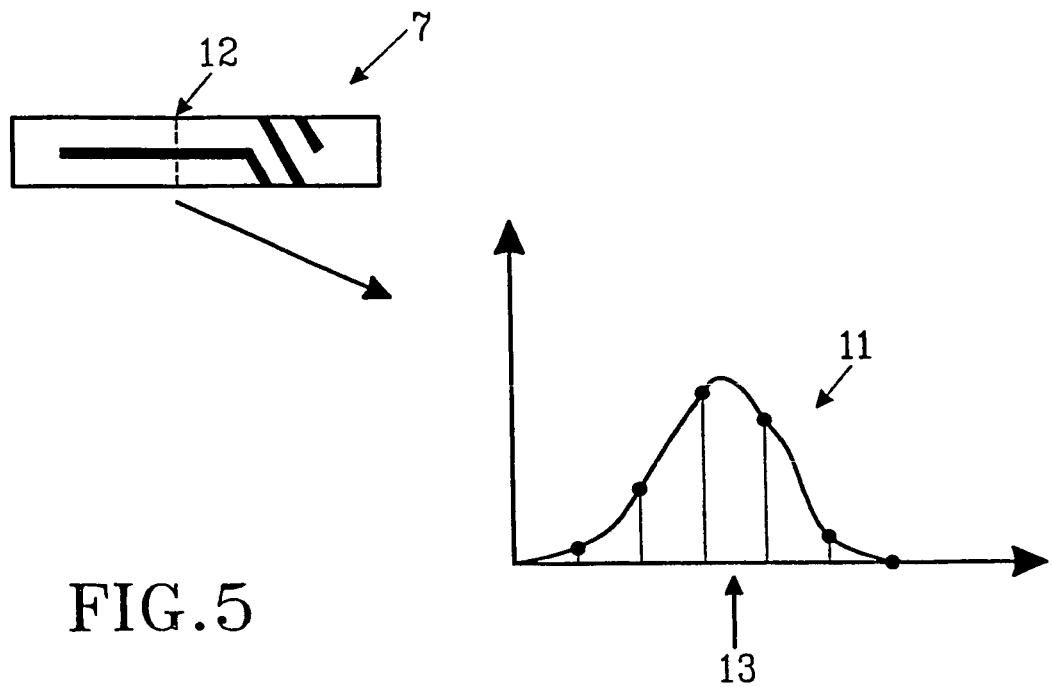
FIG. 5 shows the intensity distribution in a column of the summation image.

From the summation image it is then possible to detect in precisely which sensor row in the total image the representation of the light source was located. If the representation of the light source is assigned a magnitude and shape that extends over a plurality of sensor rows, it is also possible, by analysing the intensity distribution 13 in a given column 12, to also detect the position of the line with sub-pixel accuracy 13. Since the imaging sensor in practice comprises discrete image points, this analysis is undertaken on the basis of a series of discrete values, as illustrated in FIG. 5. Determining the position of the line with great accuracy in this way is well known, see [D3], for example, even if in the known methods this calculation is performed directly from the original image. In our case we perform the calculation on the summation image but by combining this with information from the bit field 9 we can reconstruct precisely where in the original image the line was located.

Figure 6:
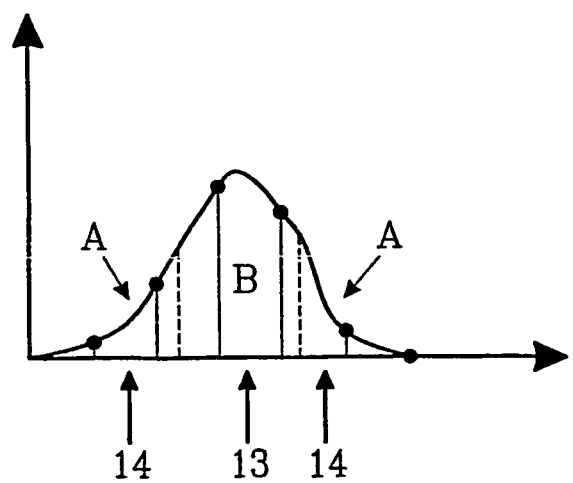
FIG. 6 shows how the intensity distribution is used in order to obtain the light scatter information.

In the same way it is also possible to measure the light scatter by studying the shape of the representation of the light source over a number of sensor rows. In a material which scatters light in the surface layer, the representation of the light source will ostensibly be wider than in a material with no light scatter. Let us assume that the detected intensity distribution has a shape like that illustrated in FIG. 5. A measure of the light scatter can thereby be obtained, for example, by directly studying the intensity in the edge areas (A in FIG. 6), or alternatively by comparing the outer areas with the middle area (B in FIG. 6), or the total intensity (A+B). One possible way of measuring the edge intensity is to proceed from the position 13 previously worked out, which may therefore lie between two sensor rows. Then, moving a predetermined distance in both directions, the edge intensities at the positions 14 are calculated, for example by interpolation. Other measured values, which vary in different ways as function of the form of the intensity distribution, are also possible, however, and the invention in no way depends on precisely how this is done.

Figure 7:
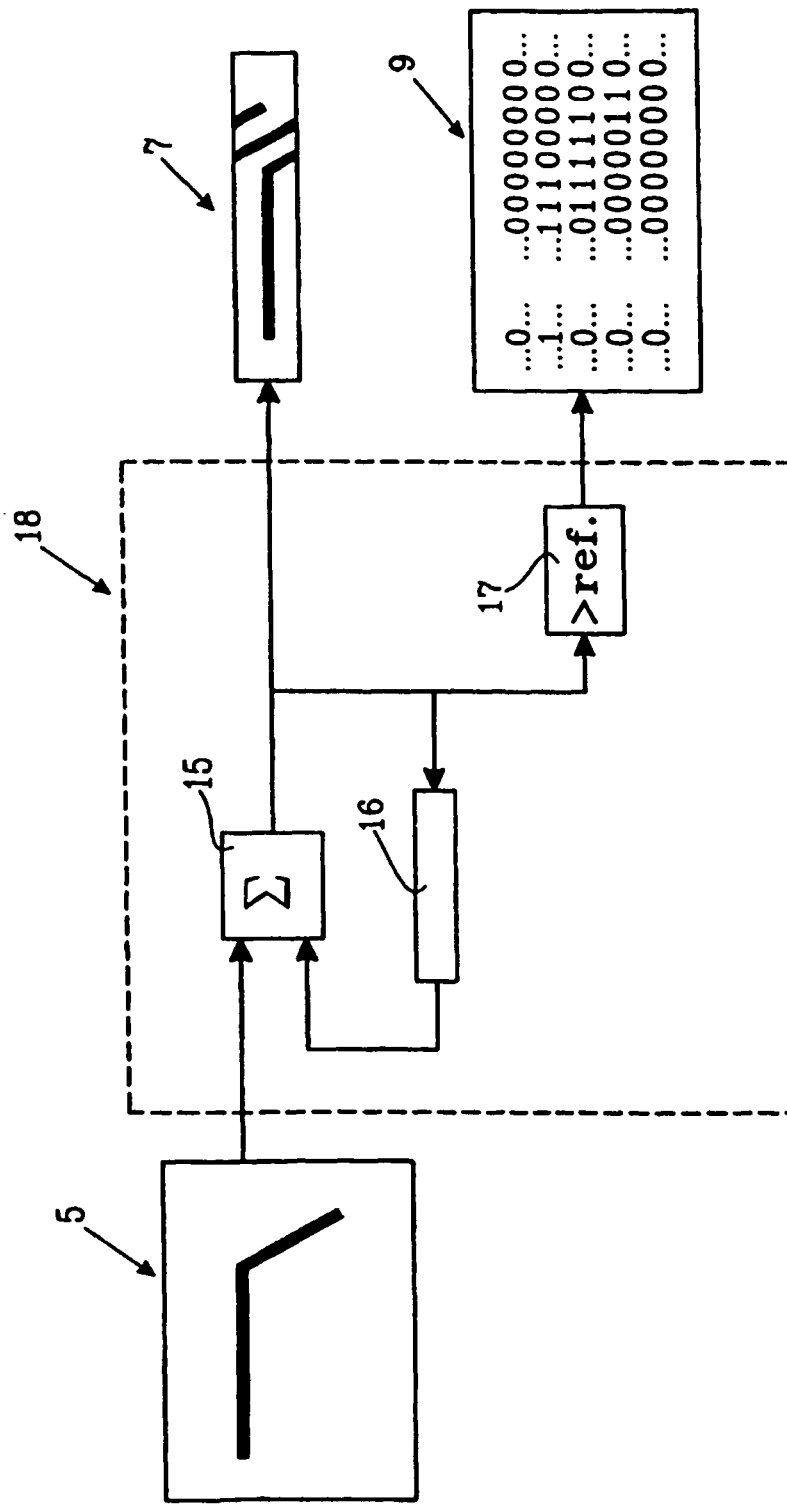
FIG. 7 shows an embodiment for generating a summation image and a decoding vector.
Figure 8:
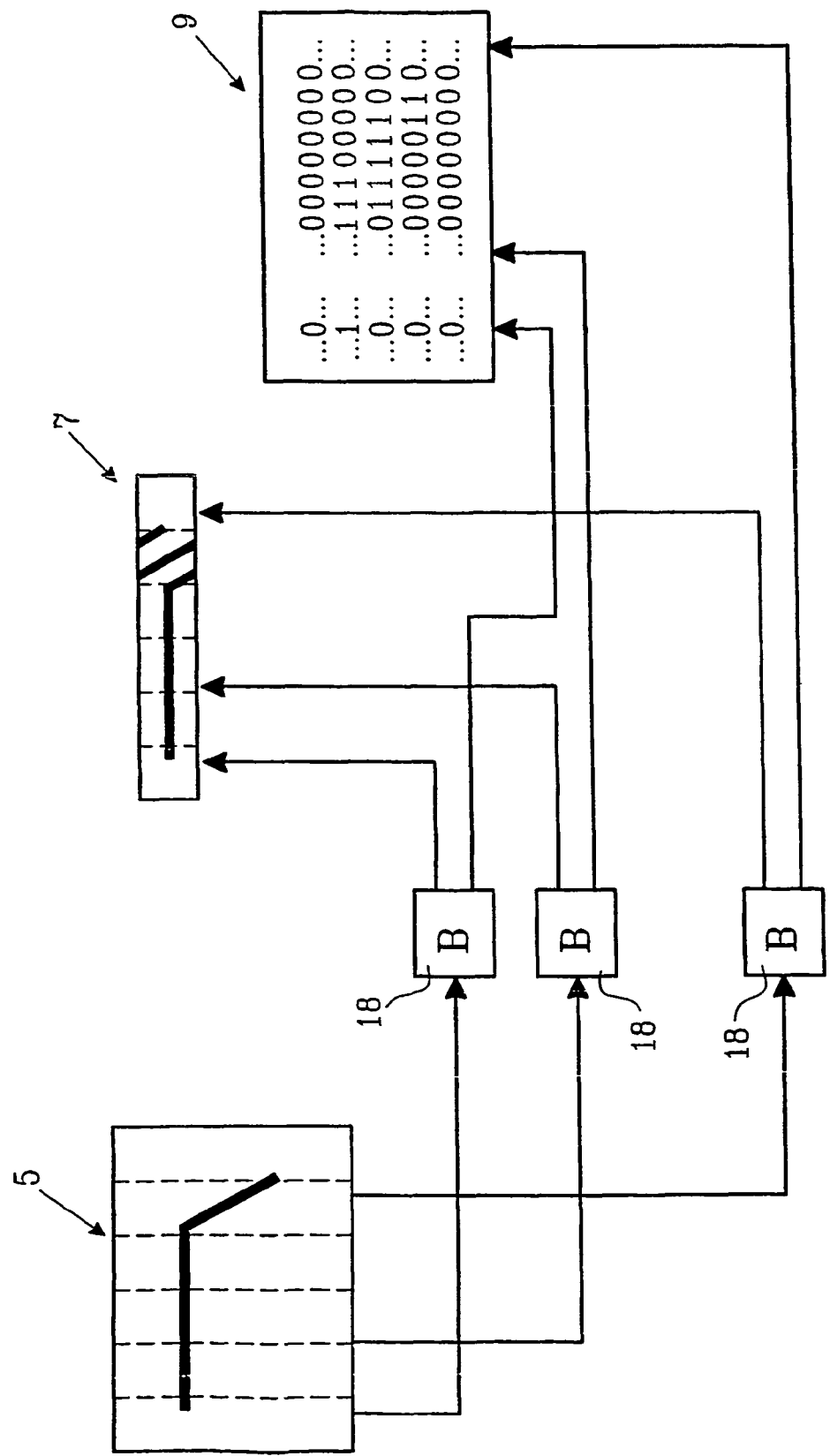
FIG. 8 shows an alternative embodiment for generating a summation image and a decoding vector.

The formation of the summation image and the detection of the position of the line can be performed in a number of different ways. One alternative is to use a conventional image-processing sensor in combination with a computer unit, for example a digital signal processor. If the image-processing sensor has the facility for reading out the sensor rows in random order, the total image and the bit field vector can advantageously be formed by electronic circuits according to FIG. 7, in which a summator 15 adds the content of the various lines, which are buffered in a line register 16 whilst a threshold circuit 17 is used for detecting the approximate position of the line. FIG. 7 is here somewhat simplified in the sense that the threshold circuit 17 ensures that only when the total exceeds the threshold for the first time is a one obtained in the result vector 9. In an advantageous embodiment an image-processing sensor having a plurality of parallel outputs is used, for example a Photobit PB1024, in which the circuits 18 in FIG. 7 are repeated with a set-up for each output as illustrated in FIG. 8. As an alternative to summation it is also possible here to use a max-operation.

In a further advantageous embodiment an image-processing sensor is used which has integrated circuits for parallel processing of image data in columns, for example MAPP2200 and MAPP2500. These circuits also afford the facility for forming the column by analog summation of data from different sensor rows. The method can thereby be performed at very high speed.

Only single-sided measurement using one light source or camera has been demonstrated above. In practice the timber will often be measured from more than one side using a measuring set-up for each side. These can either be displaced in relation to one another, so that they measure in various positions in the timber feed direction or they can be located in the same position. In the latter case it will be suitably ensured that the planes from the light sources coincide. Otherwise if the timber has an irregular shape it is possible to get interference from the light sources of the adjacent measuring units. If the light planes on either side coincide, the light sources may advantageously be placed so that a single surface is illuminated from more than one light source. For example, it is possible to turn the light sources in the plane so that they illuminate the timber from an angle of 45 degrees. This not only gives more even illumination but also greater security, since illumination is still available if one light source should fail. Neither is there anything, in the case of unilateral illumination, to prevent the use of multiple light sources from different directions within the plane in order to achieve more even illumination and increased reliability.

In the description above it is specified that the light source is linear. An alternative embodiment involves replacing the line with a series of points in one or more rows. It is likewise stated in the description that measurement is performed on a piece of timber. The invention obviously works just as well in measuring the geometric profile of and/or the light scatter in an object of some other shape or of a material other than wood. Examples of material are fibrous material such as cellulose and paper. The invention must thereby be regarded as being limited only by the scope of the patent claims below.

We claim:

1. A method for determining imaging characteristics of an object, the method comprising:
    casting incident light in a linear shape from one light source onto a specific location on an object;
    capturing detected light with one image sensor while casting the incident light, the detected light including at least (i) light from reflection of the incident light, and (ii) light from scattering of the incident light;
    generating a record associated with the specific location from the detected light, the record including at least (i) first information about the reflection of the incident light, and (ii) second information about the scattering of the incident light; and
    determining an object profile for the specific location and an object scattering property for the specific location by reading the first and second information in the record associated with the specific location.

2. The method of claim 1, wherein generating the record comprises forming a first image from the captured light.

3. The method of claim 2,
    Wherein the light source is a laser forming a line of laser light on the object;
    the first image contains a profile corresponding to the line of laser light on the object;
    the object profile is determined using the profile in the first image; and
    the object scattering property is determined using an intensity distribution of the profile in the first image.

4. The method of claim 3, wherein determining the object scattering property comprises:
    identifying a middle area and an edge area in the intensity distribution; and
    comparing an intensity in the edge area with at least an intensity in the middle area.

5. The method of claim 2, wherein generating the record further comprises processing the first image to generate a second image having a reduced data quantity compared to the first image.

6. The method of claim 5, wherein the first image includes image information distributed in rows and columns that represents at least part of the linear shape, and wherein the method further comprises:
    (i) successively selecting respective subsets of the rows;
    (ii) for each row in each of the subsets, determining whether the row's portion of the image information meets a criterion, and if so registering in the record any of the columns where the criterion is exceeded; and
    (iii) generating a representative row for each of the subsets using the image information of the rows in the respective subset, the second image formed by the representative rows and containing a version of the linear shape of the incident light.

7. The method of claim 6, wherein generating each representative row comprises:
    processing the portion of the image information of each row in the subset; and
    detecting, while processing, whether a sum of added image information for any of the columns exceeds the criterion.

8. The method of claim 7, wherein the processing comprises summing the portion of the image information of each row in the subset.

9. The method of claim 7, wherein the processing comprises performing a max operation on the portion of the image information of each row in the subset.

10. The method of claim 1, wherein the object is elongate in one direction essentially perpendicular to the linear shape of the incident light.

11. The method of claim 1, wherein at least one of the light source and the object is moving while the incident light is cast and the detected light is captured.

12. A system comprising:
    one light source casting incident light in a linear shape onto a specific location on an object;
    one image sensor capturing detected light while the incident light is being cast, the detected light including at least (i) light from reflection of the incident light, and (ii) light from scattering of the incident light; and
    an image-processing unit generating a record associated with the specific location from the detected light, the record including at least (i) first information about the reflection of the incident light, and (ii) second information about the scattering of the incident light;
    wherein the image-processing unit determines an object profile for the specific location and an object scattering property for the specific location by reading the first and second information in the record associated with the specific location.

13. The system of claim 12, wherein the record comprises a first image formed from the captured light.

14. The system of claim 13, wherein:
    the light source is a laser forming a line of laser light on the object;
    the first image contains a profile corresponding to the line of laser light on the object;

the object profile is determined using the profile in the first image; and the object scattering property is determined using an intensity distribution of the profile in the first image.

15. The system of claim 13, wherein the image-processing unit determines the object scattering property by:
   identifying a middle area and an edge area in the intensity distribution; and
   comparing an intensity in the edge area with at least an intensity in the middle area.

16. The system of claim 13, wherein the image-processing unit generates the record by processing the first image to generate a second image having a reduced data quantity compared to the first image.

17. The system of claim 16, wherein the first image includes image information distributed in rows and columns that represents at least part of the linear shape, and wherein the image-processing unit further:
   (i) successively selects respective subsets of the rows;
   (ii) for each row in each of the subsets, determines whether the row's portion of the image information meets a criterion, and if so registers in the record any of the columns where the criterion is exceeded; and
   (iii) generates a representative row for each of the subsets using the image information of the rows in the respective subset, the second image formed by the representative rows and containing a version of the linear shape of the incident light.

18. The system of claim 17, wherein in generating each representative row the image-processing unit:
   processes the portion of the image information of each row in the subset; and
   detects, while processing the portion of the image information of each row in the subset, whether a sum of added image information for any of the columns exceeds the criterion.

19. The system of claim 18, wherein the image-processing unit sums the portion of the image information of each row in the subset.

20. The system of claim 18, wherein the image-processing unit performs a max operation on the portion of the image information of each row in the subset.

21. The system of claim 12, wherein the object is elongate in one direction essentially perpendicular to the linear shape of the incident light.

22. The system of claim 12, wherein at least one of the light source and the object is moving while the light source casts the incident light and the image sensor captures the detected light.

* * * * *

UNITED STATES PATENT AND TRADEMARK OFFICE
CERTIFICATE OF CORRECTION

PATENT NO.         : 8,923,599 B2
APPLICATION NO.    : 10/774948
DATED              : December 30, 2014
INVENTOR(S)        : Anders Astrom and Erik Astrand Page 1 of 1

It is certified that error appears in the above-identified patent and that said Letters Patent is hereby corrected as shown below:

Title Page item (56),

Column 2, Line 1 (Other Publications), please delete ""Automataic" and insert -- "Automatic --, therefor.

Page 2, Column 2, Line 4 (Other Publications), please delete "DIMENSIONSMAD TNING" and insert -- DIMENSIONSMATNING --, therefor.

Page 2, Column 2, Line 21 (Other Publications), please delete "Universtiy" and insert -- University --, therefor.

In the Claims,

Column 5, Line 60, in Claim 3, please delete "Wherein" and insert -- wherein --, therefor.

Signed and Sealed this
Ninth Day of June, 2015

Michelle K. Lee
*Director of the United States Patent and Trademark Office*